(12) United States Patent
Ishii et al.

(10) Patent No.: US 6,326,520 B1
(45) Date of Patent: Dec. 4, 2001

(54) OPTICALLY ACTIVE COMPOUND AND METHOD FOR PRODUCING SAME

(75) Inventors: Akihiro Ishii, Saitama; Koichi Mikami, Yokohama, both of (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 09/377,688

(22) Filed: Aug. 20, 1999

(30) Foreign Application Priority Data

Aug. 21, 1998 (JP) .................................................. 10-236157
Aug. 21, 1998 (JP) .................................................. 10-236158
Aug. 21, 1998 (JP) .................................................. 10-236159

(51) Int. Cl.[7] .......................... C07C 49/213; C07C 45/29; C07C 43/03; C07F 7/04

(52) U.S. Cl. .......................... 568/308; 568/320; 568/335; 568/626; 568/628; 568/662; 568/663; 556/465; 556/482

(58) Field of Search .................................... 568/308, 309, 568/338, 343, 347, 364, 365, 366, 626, 320, 335, 336, 662, 628, 663; 556/465, 482

(56) References Cited

FOREIGN PATENT DOCUMENTS 11-189550    7/1999  (JP) .

Primary Examiner—Sreeni Padmanabhan
(74) Attorney, Agent, or Firm—Crowell & Moring LLP

(57) ABSTRACT

The invention relates to a method for producing a novel optically active compound represented by the general formula [IV]. This method includes the step of reacting a vinyl ether with a halogenated acetaldehyde in the presence of an optically active binaphthol-titanium complex. With this, the novel optically active compound can be produced very easily. Furthermore, the novel optically active compound can easily be oxidized to a novel optically active α,β-dihydrexyketone represented by the general formula [V]. These novel optically active compounds can each be used as useful intermediates.

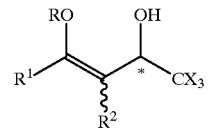

[IV]

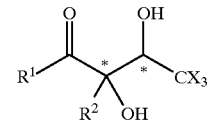

[V]

where R is a lower alkyl group or $-Si(R^3)_3$, where $R^3$ is a lower alkyl group and three of $R^3$ may be the same or different groups, $R^1$ is a lower alkyl group or a substituted or unsubstituted phenyl group, $R^2$ is hydrogen atom or a lower alkyl group or a substituted or unsubstituted phenyl group, or $R^1$ and $R^2$ are combined to form an alkylene group, and X is hydrogen, fluorine, chlorine or bromine with a proviso that three of said X may be the same or different atoms, but are not hydrogen at the same time.

17 Claims, No Drawings

OPTICALLY ACTIVE COMPOUND AND METHOD FOR PRODUCING SAME

BACKGROUND OF THE INVENTION

The present invention relates to optically active compounds, which are useful as intermediates for producing medicines, agricultural chemicals and various functional materials, and methods for producing such optically active compounds.

Japanese Patent First Provisional Publication JP-A-11-189550 discloses a method for producing an optically active Friedel-Crafts-type compound by reacting an aromatic compound (e.g., anisole) with a halogenated acetaldehyde in the presence of an optically active binaphthol-titanium complex used as a catalyst.

SUMMARY OF THE INVENTION

It is an object of the present invention to provide a novel optically active compound.

It is another object of the present invention to provide a method for easily producing such compound.

According to a first aspect of the present invention, there is provided a first method for producing an optically active compound represented by the general formula [IV]. This method comprises reacting a compound represented by the general formula [II] with a halogenated acetaldehyde represented by the general formula [III], in the presence of an optically active binaphthol-titanium complex,

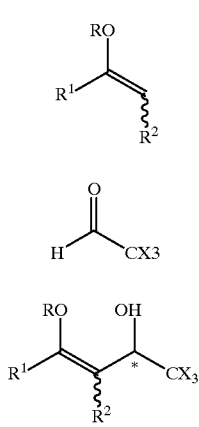

where R is a lower alkyl group or —Si($R^3$)$_3$, where $R^3$ is a lower alkyl group and three of $R^3$ may be the same or different groups, $R^1$ is a lower alkyl group or a substituted or unsubstituted phenyl group, $R^2$ is hydrogen atom or a lower alkyl group or a substituted or unsubstituted phenyl group, or $R^1$ and $R^2$ are combined to form an alkylene group, and X is hydrogen, fluorine, chlorine or bromine with a proviso that three of said X may be the same or different atoms, but are not hydrogen at the same time. In the general formula [IV] and the other formulas throughout the application, * mark represents an asymmetric carbon atom.

According to a second aspect of the present invention, there is provided a second method for producing an optically active, α,β-dihydroxyketone represented by the general formula [V]. This method comprises oxidizing a compound represented by the general formula [IV] into the optically active α,β-dihydroxyketone,

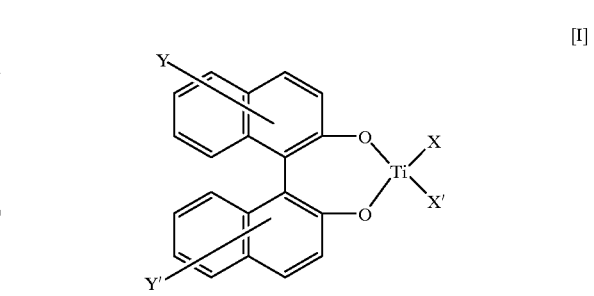

where R, $R^1$, $R^2$ and X are defined as above.

The above-mentioned optically active compounds represented by the general formulas [IV] of the first method and the optically active α,β-dihydroxyketone represented by the general formula [V] of the second method can each be used as intermediates for producing medicines, agricultural chemicals, various functional materials, etc. These aimed compounds with high optical purity can each be produced easily by the above-mentioned first and second methods.

DESCRIPTION OF THE PREFERRED EMBODIMENTS

The above-mentioned optically active binaphthol-titanium complex is used as a catalyst in the first method. This complex may have a structure represented by the following general formula [I], but is not limited to this structure.

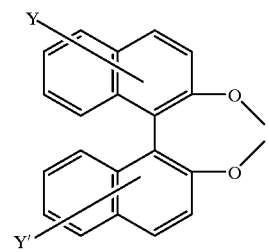

where X and X' are as a whole a group represented by the following formula or are each halogen atom, OTf, N(Tf)$_2$ or C(Tf)$_3$ where Tf represents —SO$_2$Rf where Rf is fluorine atom or a lower perfluoroalkyl group, where each of Y and Y' is hydrogen atom, halogen atom, a lower alkyl group, CN, Si($R^5$)$_3$, SO$_2R^6$, or —C≡C$R^7$, where $R^5$ is a lower alkyl group, $R^6$ is a lower alkyl group or a substituted or unsubstituted phenyl group, and $R^7$ is hydrogen atom, a lower alkyl group, a substituted or unsubstituted phenyl group, or Si($R^8$)$_3$ where $R^8$ is a lower alkyl group.

The optically active binaphthol-titanium complex used in the first method is preferably one prepared by a third method comprising the step of reacting a titanium-containing reactant with a binaphthol represented by the following general formula,

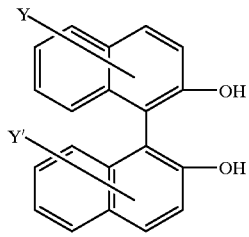

where Y, Y' R$^5$, R$^6$, R$^7$ and R$^8$ are defined as above. Upon this, the molar ratio of titanium to the binaphthol is preferably from 1/10 to 1/1, more preferably from 1/2 to 1/1. It is preferable that the titanium-containing reactant is (1) a reaction liquid obtained by reacting a tetrahalogenotitanium, of which halogens are fluorine, chlorine, bromine and/or iodine, with a lower alcohol or a titanium tetraalkoxide of lower alcohol, or (2) a titanium halogenoalkoxide of lower alcohol, for example, dialkoxydihalogenotitanium or diisopropoxydihalogenotitanium, of which halogens are flourine, chlorine, bromine and/or iodine. Examples of this lower alcohol are methanol, ethanol, n-propanol, isopropanol, n-butanol, sec-butanol, and tert-butanol. Of these, isopropanol is the most preferable. The step of the third method for preparing the complex is conducted preferably in a solvent in the presence of a zeolite. This zeolite may be selected from various synthetic zeolites. Of these, it is preferable to select one from A-type zeolites, such as 3A, 4A and 5A, and X-type zeolites, such as 13X. The solvent used in the third method is not particularly limited, and can be selected from halogenated hydrocarbons such as methylene chloride, chloroform, carbon tetrachloride and dichloroethane; aromatic hydrocarbons such as benzene, toluene, xylene and ethylbenzene; ethers such as dimethyl ether, diethyl ether, tetrahydrofuran and diglyme; and nitriles such as acetonitrile and propionitrile.

For example, the third method for preparing an optically active binaphthol-titanium complex may be conducted as follows. At first, a dialkoxydihalogenotitanium is prepared by reacting at least one tetrahalogenotitanium (e.g., tetrafluorotitanium, tetrachlorotitanium, tetrabromotitanium and/or tetraiodotitanium) with tetraisopropoxytitanium in methylene chloride (solvent). Then, the complex is prepared by reacting this dialkoxydihalogenotitanium with an optically active binaphthol in the presence of a zeolite, molecular sieve (MS) 4A. Optically active binaphthol (BINOL) has two types, that is, one type of S-configuration ((S)-BINOL) and another type of R-configuration ((R)-BINOL). Thus, the obtained complex also has one type of S-configuration and another type of R-configuration. One of these two types of the complex can be chosen according to the absolute configuration of the aimed product of the first method.

Nonlimitative examples of the halogenated acetaldehyde represented by the general formula [III] are trifluoroacetaldehyde (fluoral), chlorodifluoroacetaldehyde, bromodifluoroacetaldehyde, dichlorofluoroacetaldehyde, bromochlorofluoroacetaldehyde, dibromofluoroacetaldehyde, trichloroacetaldehyde, bromodichloroacetaldehyde, dibromochloroacetaldehyde, tribromoacetaldehyde, difluoroacetaldehyde, chlorofluoroacetaldehyde, bromofluoroacetaldehyde, dichloroacetoaldehyde, bromochloroacetaldehyde, dibromoacetaldehyde, fluoroacetaldehyde, chloroacetaldehyde, and bromoacetaldehyde. In the invention, these halogenated acetaldehydes may be replaced with their hydrates or hemiacetals.

The reaction of the first method is an equimolar Friedel-Crafts reaction. Therefore, it is preferable to use the halogenated acetaldehyde in an amount of at least 1 mole, more preferably of 1–100 moles, still more preferably of 1–10 moles, per mole of the compound represented by the general formula [II].

In the first method, the amount of the optically active binaphthol-titanium complex, which is used as an asymmetric catalyst, is not particularly limited. Its amount is preferably 0.1–50 mol %, more preferably 0.1–30 mol %, still more preferably 0.1–10 mol %, based on the total moles of the compound represented by the general formula [II].

Although solvent may not be used in the reaction of the first method, it is preferably used therein. Examples of this solvent are halogenated hydrocarbons such as methylene chloride, chloroform, and carbon tetrachloride; aromatic hydrocarbons such as benzene, toluene, xylene and ethylbenzene; ethers such as tetrahydrofuran, diethyl ether, and dioxane; and esters such as ethyl acetate. The reaction of the first method is conducted at a temperature of preferably from −50 to 50° C., more preferably from −30 to 30° C., still more preferably from −10 to 10° C.

In each of the first and second methods, a crude product can be obtained by conducting a conventional post-treatment after the reaction. According to need, the obtained crude products can be purified, for example, by recrystallization, column chromatography, etc., to respectively obtain the aimed optically active compounds represented by the general formulas [IV] and [V], with high yield and high optical purity.

In the third method, the oxidation may be conducted by using an oxidizing agent. Examples of the oxidizing agent are methachloroperbenzoic acid (m-CPBA), trifluoroperacetic acid, hydrogen peroxide, a combination of hydrogen peroxide and acetic acid, t-butylperoxide, benzoylperoxide, t-butyl perbenzoate, t-butyl peracetate, cumene hydroperoxide, t-butyl hydroperoxide (TBHP), triphenylmethyl hydroperoxide, potassium permanganate, chromic acid, potassium chromate, pyridinium chlorochromate (PCC), osmium oxide, ruthenium oxide, and molybdenum oxide. These oxidizing agents are used in combination, that is, VO(acac)$_2$/TBHP, MoO$_3$[ON(C$_6$H$_5$)Bz]/TBHP, Ti(O-i-Pr)$_4$/TBHP, and Al(O-t-Bu)$_3$/TBHP. Furthermore, the oxidation may be conducted by using oxygen or ozone. The oxidizing agent is in an amount of preferably at least one equivalent, more preferably 1–3 equivalents, still preferably 1–2 equivalents, per equivalent of the compound represented by the formula [IV]. It is preferable to use a solvent in the oxidation of the third method. Examples of this solvent are water; alcohols such as methanol, ethanol and propanol; halogenated hydrocarbons such as methylene chloride, chloroform, and carbon tetrachloride; aromatic hydrocarbons such as benzene, toluene and xylene; ethers such as tetrahydrofuran, diethyl ether, and dioxane; and ketones such as acetone. It is possible to proceed the oxidation of the third method with a sufficient reaction rate at about room temperature. Furthermore, it is able to proceed efficiently under heated condition and even under cooled condition (e.g., at about 0° C.).

The following nonlimitative examples are illustrative of the present invention. In fact, Examples 1-1, 1-2, 1-3, 1-4, 1-5, 1-6 and 1-7 are illustrative of the first method of the invention.

EXAMPLE 1-1

An optically active binaphthol-titanium complex was prepared as follows. At first, 368 mg (1.287 mmol) of binaphthol of R-configuration ((R)-BINOL), 305 mg (1.287 mmol) of diisopropoxydichlorotitanium (TiCl$_2$(O-i-Pr)$_2$), and 6.43 g of molecular sieve 4A (MS4A) were added to 12.9 ml of methylene chloride (solvent). This mixture was stirred for 1 hr at room temperature in an atmosphere of argon. After that, 20 ml of toluene was added to the mixture, followed by centrifugation and then cerite filtration. The filtrate was evaporated to dryness under reduced pressure, thereby obtaining a binaphthol-titanium complex of R-configuration ((R)-BINOL-Ti catalyst).

Then, 19.7 mg (0.049 mmol, 0.2 eq) of (R)-(BINOL-Ti catalyst and 39.9 mg (0.246 mmol, 1.0 eq, E/Z=1/1) of a vinyl ether represented by the following formula were added to 1.48 ml of methylene chloride.

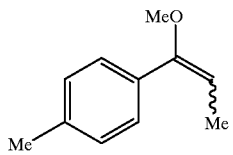

Then, an excessive amount of fluoral (trifluoroacetaldehyde) was bubbled into the mixture under cooling with ice in an atmosphere of argon, followed by stirring for 30 min at the same temperature as that of the bubbling. After the stirring, water was added to the mixture. Then, methylene chloride was added to the mixture for solvent extraction, followed by drying with anhydrous magnesium sulfate and then its concentration, thereby obtaining a crude reaction product. This crude reaction product was subjected to a silica gel column chromatography (methylene chloride:hexane =3:2), thereby obtaining a Friedel-Crafts-type product (yield: 64%, E/Z=5/1, enantiomeric excess (e. e.) of the E-configuration product: 85% e.e. (R-configuration)) represented by the following formula.

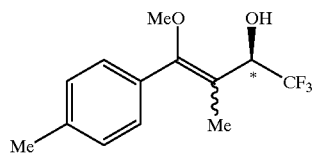

The above product was subjected to $^1$H-NMR (TMS, ppm, CDCl$_3$), and the results are as follows:

E-configuration product: 7.2 (4H, m, aromatic), 4.9 (1H, q, CF$_3$C$\underline{H}$OH), 3.8 (1H, d, CF$_3$CHO$\underline{H}$), 3.3 (3H, s, C$\underline{H}_3$O), 2.4 (3H, s, C$\underline{H}_3$-aromatic), and 1.7 (3H, s, vinylic-C$\underline{H}_3$); and Z-configuration product: 7.2 (4H, m, aromatic), 4.4 (1H, q, CF$_3$C$\underline{H}$OH), 3.3 (3H, s, C$\underline{H}_3$O), 2.4 (3H, s, C$\underline{H}_3$-aromatic), 2.0 (1H, d, CF$_3$CHO$\underline{H}$), and 1.9 (3H, s, vinylic-C$\underline{H}_3$).

The above-mentioned enantiomeric excess of the E-configuration product was determined by the chiral high performance liquid chromatography (HPLC) of the acid hydrolysis product under the following conditions of the chiral HPLC:

Daicel, CHIRALPAK AS, hexane:isopropanol=98:2, 0.8 ml/min, 254 nm, and retention time; threo/S:11 min, R:38 min, erythro/R:14 min and S:25 min.

EXAMPLE 1-2

AT first, 9.9 mg (0.025 mmol, 0.1 eq) of (R)-BINOL-Ti catalyst, which is the same as that of Example 1-1, and 33.0 mg (0.246 mmol, 1.0 eq) of a vinyl ether represented by the following formula were added to 1.48 ml of methylene chloride.

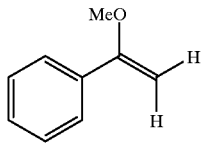

Then, an excessive amount of fluoral was bubbled into the mixture under cooling with ice in an atmosphere of argon, followed by stirring for 30 min at the same temperature as that of the bubbling. After the stirring, water was added to the mixture. Then, methylene chloride was added to the mixture for solvent extraction, followed by drying with anhydrous magnesium sulfate and then its concentration, thereby obtaining a crude reaction product. This crude reaction product was subjected to a silica gel column chromatography (methylene chloride:hexane=3:2), thereby obtaining a Friedel-Crafts-type product (yield:54%, E/Z=1/2, enantiomeric excess of the mixture of E- and Z-configuration product (E/Z=1/2): 72% e.e. (R-configuration)) represented by the following formula.

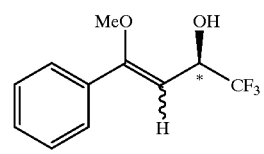

The above product was subjected to $^1$H-NMR (TMS, ppm, CDCl$_3$), and the results are as follows:

Z-configuration product: 7.4 (5H, m, aromatic), 4.8 (1H, d, vinylic-$\underline{H}$), 4.5 (1H, m, CF$_3$C$\underline{H}$OH), 3.8 (3H, s, C$\underline{H}_3$O), and 2.0 (1H, d, CF$_3$CHO$\underline{H}$); and E-configuration product: 7.4 (5H, m, aromatic), 5.2 (1H, d, vinylic-$\underline{H}$), 5.0 (1H, m, CF$_3$C$\underline{H}$OH), 3.6 (3H, s, C$\underline{H}_3$O), 2.9 (1H, d, CF$_3$CHO$\underline{H}$).

The above-mentioned enantiomeric excess of the mixture of E- and Z-configuration product (E/Z=2/3) was determined by the chiral HPLC of the acid hydrolysis product under the following conditions of the chiral HPLC:

Daicel, CHIRALPAK OD-H, hexane:isopropanol=95:5, 0.8 ml/min, 254 nm, and retention time; S:12 min and R:14 min.

EXAMPLE 1-3

At first, 27.0 mg (0.049 mmol, 0.2 eq) of (R)-6,6'-Br$_2$-BNOL-Ti catalyst, which was prepared in a manner substantially the same as that for preparing (R)-BINOL-Ti catalyst of Example 1-1 using (R)-(-)-6,6'-dibromo-1,1'-bi-2-naphthol in place of binaphthol, and 33.0 mg (0.246 mmol, 1.0 eq) of a vinyl ether represented by the following formula were added to 1.48 ml of methylene chloride.

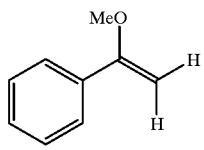

Then, an excessive amount of fluoral was bubbled into the mixture under cooling with ice in an atmosphere of argon, followed by stirring for 30 min at the same temperature as that of the bubbling. After the stirring, water was added to the mixture. Then, methylene chloride was added to the mixture for solvent extraction, followed by drying with anhydrous magnesium sulfate and then its concentration, thereby obtaining a crude reaction product. This crude reaction product was subjected to a silica gel column chromatography (methylene chloride:hexane=3:2), thereby obtaining a Friedel-Crafts-type product (yield: 48%, E/Z= 1/2, enantiomeric excess of the mixture of E- and Z-configuration product: 58% e.e. (R-configuration)) represented by the following formula.

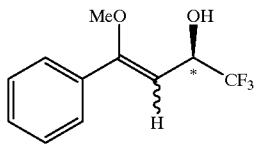

The above product was subjected to $^1$H-NMR (TMS, ppm, CDCl$_3$), and the results are as follows:

E-configuration product: 7.4 (5H, m, aromatic), 4.8 (1H, d, vinylic-$\underline{H}$), 4.5 (1H, m, CF$_3$C$\underline{H}$OH), 3.8 (3H, s, C$\underline{H_3}$O), and 2.0 (1H, d, CF$_3$CHO$\underline{H}$); and Z-configuration product: 7.4 (5H, m, aromatic), 5.2 (1H, d, vinylic-$\underline{H}$), 5.0 (1H, m, CF$_3$C$\underline{H}$OH), 3.6 (3H, s, C$\underline{H_3}$O), and 2.9 (1H, d, CF$_3$CHO$\underline{H}$).

The above-mentioned enantiomeric excess of the E-configuration product was determined by the chiral HPLC of the acid hydrolysis product under the following conditions of the chiral HPLC:

Daicel, CHIRALPAK OD-H, hexane:isopropanol=95:5, 0.8 ml/min, 254 nm, and retention time; S12 min and R:14 min.

EXAMPLE 1-4

At first, 25.3 mg (0.063 mmol, 0.2 eq) of (R)-BINOL-Ti catalyst, which was prepared in the same manner as that of Example 1-1, and 82.9 mg (0.316 mmol, 1.0 eq) of a silylenol ether represented by the following formula were added to 1.90 ml of methylene chloride.

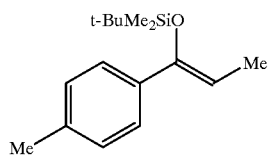

Then, an excessive amount of floural was bubbled into the mixture under cooling with ice in an atmosphere of argon, followed by stirring for 30 min at the same temperature as that of the bubbling. After the stirring, water was added to the mixture. Then, methylene chloride was added to the mixture for solvent extraction, followed by drying with anhydrous magnesium sulfate and then its concentration, thereby obtaining a crude reaction product. This crude reaction product was subjected to a silica gel column chromatography (methylene chloride:hexane=3:2), thereby obtaining a Friedel-Crafts-type product (yield: 77%, E/Z= 1/6, enantiomeric excess of the Z-configuration product: 94% e.e. (R-configuration) and enantiomeric excess of the E-configuration product: 66% e.e. (R-configuration)) represented by the following formula.

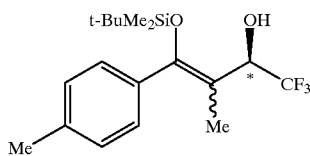

The above product was subjected to $^1$H-NMR (TMS, ppm, CDCl$_3$), and the results are as follows:

Z-configuration product: 7.2 (4H, m, aromatic), 4.6 (1H, q, CH$_3$C$\underline{H}$OH), 2.4 (3H, s, C$\underline{H_3}$-aromatic), 2.0 (1H, d, CF$_3$CHO$\underline{H}$), 1.8 (3H, s, vinylic-C$\underline{H_3}$), 0.9 (9H, s, Si $\underline{t}$-$\underline{B}$uMe$_2$), −0.16(3H, s, Sit-Bu$\underline{Me_2}$), and −0.24(3H, s, Sit-Bu $\underline{Me_2}$); and E-configuration product 7.2 (4H, m, aromatic), 5.3 (1H, q, CF$_3$C$\underline{H}$OH), 2.7 (1H, d, CF$_3$CHO$\underline{H}$), 2.4 (3H, s, C $\underline{H_8}$-aromatic), 1.6 (3H, s, vinylic-C$\underline{H_3}$), 0.9 (9H, s, Si $\underline{t}$-$\underline{B}$uMe$_2$), and −0.2(6H, s, Sit-B$\underline{uMe_2}$).

The above-mentioned enantiomeric excess of the Z-configuration and E-configuration products were determined by the chiral HPLC of the acid hydrolysis product under the following conditions of the chiral HPLC:

Daicel, CHIRALPAK AS, hexane:isopropanol=98:2, 0.8 ml/min, 254 nm, and retention time; threo/S:11 min, R:38 min, erythro/R:14 min and S:25 min.

EXAMPLE 1-5

At first, 12.9 mg (0.032 mmol, 0.1 eq) of (R)-BINOL-Ti catalyst, which was prepared in the same manner as that of Example 1-1, and 75.5 mg (0.323 mmol, 1.0 eq) of a silylenol ether represented by the following formula were added to 1.94 ml of methylene chloride.

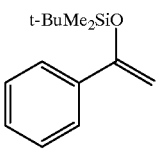

Then, an excessive amount of floural was bubbled into the mixture under cooling with ice in an atmosphere of argon, followed by stirring for 30 min at the same temperature as that of the bubbling. After the stirring, water was added to the mixture. Then, methylene chloride was added to the mixture for solvent extraction, followed by drying with anhydrous magnesium sulfate and then its concentration, thereby obtaining a crude reaction product. This crude reaction product was subjected to a silica gel column chromatography (methylene chloride:hexane=3:2), thereby obtaining a Friedel-Crafts-type product (yield: 34%, E/Z= 1/4, enantiomeric excess of the Z-configuration product: 98% e.e. (R-configuration) and enantiomeric excess of the E-configuration product: 80% e.e. (R-configuration)) represented by the following formula.

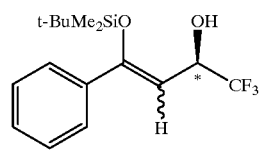

The above product was subjected to $^1$H-NMR (TMS, ppm, CDCl$_3$), and the results are as follows:

Z-configuration product: 7.3–7.5 (5H, m, aromatic), 5.1 (1H, d, vinylic-CH), 4.5 (1H, d-quin, CF$_3$CHOH), 2.0 (1H, d, CF$_3$CHOH), 0.9 (9H, s, Si t-BuMe$_2$), and 0.1 (3H*2, s*2, Sit-BuMe$_2$); and E-configuration product: 7.3–7.5 (5H, m, aromatic), 5.2 (1H, d, vinylic-CH), 5.0 (1H, d-quin, CF$_3$CHOH), 2.2 (1H, d, CF$_3$CHOH), 1.0 (9H, s, Si t-BuMe$_2$), 0.0 (3H, s, Sit-Bu Me$_2$), and −0.1 (3H, s, Sit-BuMe$_2$).

The above-mentioned enantiomeric excess of the Z-configuration and E-configuration products were determined by the chiral HPLC of the acid hydrolysis product under the following conditions of the chiral HPLC:

Daicel, CHIRALPAK OD-H, hexane:isopropanol=95:5, 0.8 ml/min, 254 nm, and retention time; S:12 min, and R:14 min.

EXAMPLE 1-6

At first, 9.1 mg (0.023 mmol, 0.01 eq) of (R)-BINOL-Ti catalyst, which was prepared in the same manner as that of Example 1-1, and 623.2 mg (2.258 mmol, 1.0 eq) of a compound represented by the following formula were added to 14.5 ml of methylene chloride.

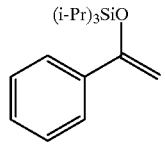

Then, an excessive amount of fluoral was bubbled into the mixture under cooling with ice in an atmosphere of argon, followed by stirring for 30 min at the same temperature as that of the bubbling. After the stirring, a saturated sodium hydrogencarbonate aqueous solution was added to the mixture. Then, methylene chloride was added to the mixture for solvent extraction, followed by drying with anhydrous magnesium sulfate and then its concentration, thereby obtaining a crude reaction product. This crude reaction product was subjected to a silica gel column chromatography (ethyl acetate:hexane=1:10), thereby obtaining a Friedel-Crafts-type product (yield: 90%, Z/E=5/1, enantiomeric excess of the Z-configuration product: 96% e.e. (R-configuration)) represented by the following formula.

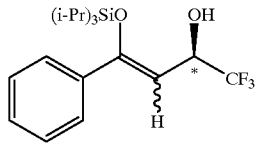

The above product was subjected to $^1$H-NMR (TMS, ppm, CDCl$_3$), and the results are as follows:

E-configuration product: 7.4–7.5 (2H, m), 7.3–7.4 (3H, m), 5.0–5.1 (2H, m), 2.1 (1H, d), and 1.0–1.1 (21H, m); and Z-configuration product: 7.5 (2H, m), 7.4 (3H, m), 5.1 (1H, d), 4.5 (1H, m), 2.0 (1H, d), 1.2 (3H, m), and 1.1 (9H*2, d*2).

The above-mentioned enantiomeric excess of the E-configuration product was determined by the chiral HPLC of the acid hydrolysis product under the following conditions of the chiral HPLC:

Daicel, CHIRALPAK OD-H, hexane:isopropanol=95:5, 0.8 ml/min, 254 nm, and retention time; S:12 min, and R:14 min.

EXAMPLE 1-7

At first, 80.6 mg (0.2 mmol, 0.2 eq) of (R)-BINOL-Ti catalyst, which was prepared in the same manner as that of Example 1-1, and 112 mg (1 mmol, 1.0 eq, E/Z=1/1) of a vinyl ether represented by the following formula were added to 6 ml of methylene chloride.

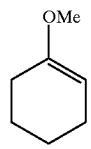

Then, an excessive amount of fluoral was bubbled into the mixture under cooling with ice in an atmosphere of argon, followed by stirring for 30 min at the same temperature as that of the bubbling. After the stirring, water was added to the mixture. Then, methylene chloride was added to the mixture for solvent extraction, followed by drying with anhydrous magnesium sulfate and then its concentration, thereby obtaining a crude reaction product. This crude reaction product was subjected to a silica gel column chromatography (methylene chloride:hexane=3:2), thereby obtaining a Friedel-Crafts-type product (yield: 52%, Z: 100%, enantiomeric excess: 43% e.e. (R-configuration)) represented by the following formula.

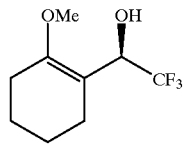

The above product was subjected to $^1$H-NMR (TMS, ppm, CDCl$_3$), and the results are as follows:

4.6 (1H, quin), 3.9 (1H, d), 3.6 (3H, s), 1.9–2.3 (4H, m), and 1.4–1.9 (4H, m).

The following Examples 2-1, 2-2 and 2-3 are illustrative of the second method of the invention.

EXAMPLE 2-1

At first, 24.3 mg (0.093 mmol, 1 eq) of a compound represented by the following formula, which was prepared by the same method as that of Example 1-1, and 40.4 mg (0.187 mmol, 2.0 eq) of m-CPBA (purity: 80%) were added to 2 ml of methanol.

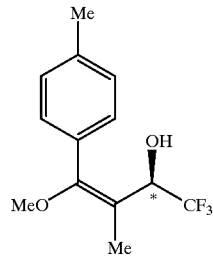

Then, the mixture was stirred for 2 hr at room temperature. After the stirring, the solvent was distilled away under reduced pressure. Then, a saturated sodium hydrogencarbonate aqueous solution was added to the residue, followed by extraction with methylene chloride, then drying with anhydrous magnesium sulfate, and then its concentration.

After that, methanol, water and an excessive amount of p-toluenesulfonic acid were added to the concentrate, followed by stirring for 30 min under reflux. The obtained reaction mixture was cooled down, followed by extraction with methylene chloride, then drying with anhydrous magnesium sulfate and then its concentration, thereby to obtain a crude product of a compound (yield: 80%) represented by the following formula:

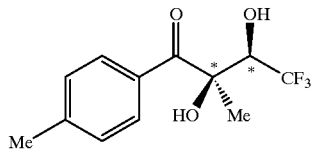

This crude product was subjected to $^1$H-NMR and $^{19}$F-NMR and HPLC to determine the diastero-selectivity. With this, diastereomer other than threo form were not found. In fact, diastereomeric excess (d. e.) was not lower than 95%. The results of $^1$H-NMR are as follows:

threo from: 7.9 (2H, d, aromatic), 7.3 (2H, d, aromatic), 4.6 (1H, dq, CF$_3$CHOH), 4.5 (1H, s, CMeOH), 3.2 (1H, d, CF$_3$CHOH), 2.4 (3H, s, CH$_3$-aromatic), and 1.7 (3H, q, CMeOH). The optical purity was not reduced by the oxidation of the second method. The enantiomeric excess of the threo form was determined by the chiral HPLC under the following conditions:

Daicel, CHIRALPAK AS, hexane:isopropanol=95.5, 0.8 ml/min, 254 nm, and retention time; R—R: 15 min and S—S: 23 min.

EXAMPLE 2-2

At first, 12.1 mg (0.034 mmol, 1 eq) of Z-configuration product of Example 1-4 and 14.5 mg (0.067 mmol, 2.0 eq) of m-CPBA (purity:80%) were added to 2 ml of methanol. Then, the mixture was stirred for 2 hr at room temperature. After the stirring, the solvent was distilled away under reduced pressure. Then, a saturated sodium hydrogencarbonate aqueous solution was added to the residue, followed by extraction with methylene chloride, then drying with anhydrous magnesium sulfate, and then its concentration, thereby obtaining a crude product of a compound (yield: 60%) represented by the following formula.

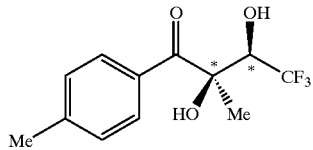

This crude product was subjected to $^1$H-NMR and $^{19}$F-NMR and HPLC to determine the diastereo-selectivity. With this, diastereomer other than threo form were not found. In fact, diastereomeric excess (d. e.) was not lower than 95%. The results of $^1$H-NMR are as follows:

threo form: 7.9 (2H, d, aromatic), 7.3 (2H, d, aromatic), 4.6 (1H, dq, CF$_3$CHOH), 4.5 (1H, s, CMeOH), 3.2 (1H, d, CF$_3$CHOH), 2.4 (3H, s, CH$_3$-aromatic), and 1.7 (3H, q, CMeOH). The optical purity was not reduced by the oxidation of the second method. The enantiomeric excess of the threo form was determined by the chiral HPLC under the following conditions:

Daicel, CHIRALPAK AS, hexane:isopropanol=95:5, 0.8 ml/min, 254 nm, and retention time; R—R: 15 min and S—S: 23 min.

EXAMPLE 2-3

At first, 6.9 mg (0.21 mmol, 1 eq) of the reaction product (E/Z=1/4) of Example 1-5 and 9.0 mg (0.042 mmol, 2.0 eq) of m-CPBA (purity: 80%) were added to 2 ml of methanol. Then, the mixture was stirred for 2 hr at room temperature. After the stirring, the solvent was distilled away under reduced pressure. Then, a saturated sodium hydrogencarbonate aqueous solution was added to the residue, followed by extraction with methylene chloride, then drying with anhydrous magnesium sulfate, and then its concentration. After that, methanol, water and an excessive amount of p-toluenesulfonic acid were added to the concentrate, followed by stirring for 30 min under reflux. The obtained reaction mixture was cooled down, followed by extraction with methylene chloride, then drying with anhydrous magnesium sulfate and then its concentration, thereby to obtain a crude product of a compound (yield: 65%) represented by the following formula.

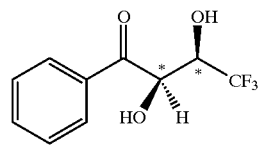

This crude product was subjected to $^1$H-NMR and $^{16}$F-NMR and HPLC to determine the diastereo-selectivity. With this, diastereomer other than threo form were not found. In fact, diastereomeric excess (d. e.) was not lower than 95%. The results of $^1$H-NMR are as follows:

threo form: 7.9 (2H, d, aromatic), 7.7 (1H, t, aromatic), 7.6 (2H, t, aromatic), 5.4 (1H, d, CHOH), 4.3 (1H, dq, CF$_3$CHOH), 4.3 (1H, d, CHOH), and 3.1 (1H, d, CF$_3$CHOH).

The entire disclosure of Japanese Patent Application Nos. 10-236157, 10-236158 and 10-236159, of which priorities are claimed in the present application, including specification, claims, and summary, is incorporated herein by reference in its entirety.

What is claimed is:

1. A method for producing an optically active compound represented by the general formula [IV], said method comprising:

reacting a compound represented by the general formula [II] with a halogenated acetaldehyde represented by the general formula [III], in the presence of an optically active binaphthol-titanium complex,

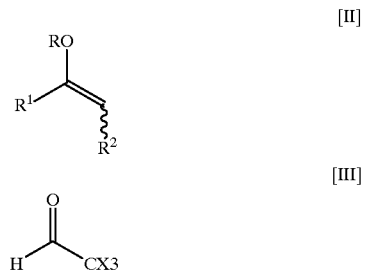

-continued

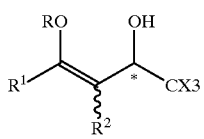

[IV]

wherein R is a lower alkyl group or —Si(R$^3$)$_3$,
R$^3$ is a lower alkyl group and three of R$^3$ may be the same of different groups,
R$^1$ is a lower alkyl group or a substituted or unsubstituted phenyl group,
R$^2$ is hydrogen atom or a lower alkyl group or a substituted or unsubstituted phenyl group, or R$^1$ and R$^2$ are combined to form an alkylene group so that the compounds represented by general formula and are cycloalkylenes, and
X is hydrogen, fluorine, chlorine or bromine with a proviso that three of said X may be the same or different atoms, but are not hydrogen at the same time.

2. A method according to claim 1, wherein said optically active binaphthol-titanium complex is represented by the general formula,

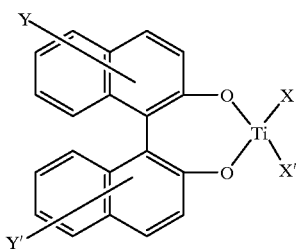

[I]

where X and X' are as a whole a group represented by the following formula or are each halogen atom, OTf, N(Tf)$_2$ or C(Tf)$_3$ where Tf represents —SO$_2$Rf where Rf is fluorine atom or a lower perfluoroalkyl group,

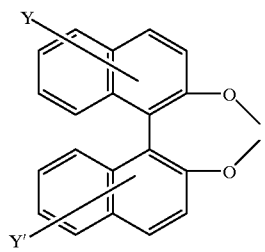

where each of Y and Y' is hydrogen atom, halogen atom, a lower alkyl group, CN, Si(R$^6$)$_3$, SO$_2$R$^6$, or —C≡CR$^7$, where R$^5$ is a lower alkyl group, R$^6$ is lower alkyl group or a substituted or unsubstituted phenyl group, and R$^7$ is hydrogen atom, a lower alkyl group, a substituted or unsubstituted phenyl group, or Si(R$^8$)$_3$ where R$^8$ is a lower alkyl group.

3. A method according to claim 1, wherein said optically active binaphthol-titanium complex is prepared by reacting a titanium-containing reactant with a binaphthol represented by the following general formula,

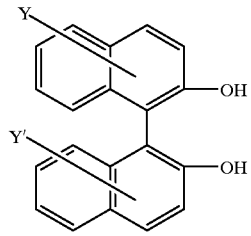

where each of Y and Y' is hydrogen atom, halogen atom, a lower alkyl group, CN, Si(R$^5$)$_3$, SO$_2$R$^6$, or —C≡CR$^7$, where R$^5$ is a lower alkyl group, R$^6$ is a lower alkyl group or a substituted or unsubstituted phenyl group, and R$^7$ is hydrogen atom, a lower alkyl group, a substituted or unsubstituted phenyl group, or Si(R$^8$)$_8$ where R$^8$ is a lower alkyl group.

4. A method according to claim 3, wherein said titanium-containing reactant is (1) a reaction liquid obtained by reacting a tetrahalogenotitanium, of which halogens are fluorine, chlorine, bromine and/or iodine, with a lower alcohol or a titanium tetraalkoxide of a lower alcohol, or (2) or titanium halogenoalkoxide of a lower alcohol, of which halogens are flourine, chlorine, bromine and/or iodine.

5. A method according to claim 4, wherein said lower alcohol is isopropanol, said titanium tetraalkoxide is tetraisopropoxytitanium, and said titanium halogenoalkoxide is diisopropoxydihalogenotitanium.

6. A method according to claim 3, wherein said optically active binaphthol-titanium complex is prepared by reacting said titanium-containing reactant with said binaphthol in the presence of a zeolite.

7. A method according to claim 5, wherein said zeolite is 4A type zeolite.

8. A method according to claim 3, wherein said optically active binaphthol-titanium complex is prepared by reacting in a solvent said titanium-containing reactant with said binaphthol.

9. A method according to claim 1, wherein said halogenated acetaldehyde is trifluoroacetaldehyde.

10. A method according to claim 1, wherein said halogenated acetaldehyde is in an amount of at least 1 mole per mole of said compound represented by the general formula.

11. A method according to claim 1, wherein said reacting is conducted at a temperature of from −50 to 50° C.

12. An optically active compound represented by the general formula [IV],

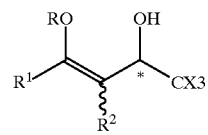

[IV]

wherein R is a lower alkyl group or —Si(R$^3$)$_3$,
R$^3$ is a lower alkyl group and three of R$^3$ may be the same or different groups,
R$^1$ is a lower alkyl group or a substituted or unsubstituted phenyl group,
R$^2$ is hydrogen atom or a lower alkyl group or a substituted or unsubstituted phenyl group, or R$^1$ and R$^2$ are combined to form an alkylene group so that the compound represented by the general formula [IV] is a cycloalkylene, and X is hydrogen, fluorine, chlorine or bromine with a proviso that three of said X may be the same or different atoms, but are not hydrogen at the same time.

13. A method for producing an optically active α,β-dihydroxyketone represented by the general formula [V], said method comprising:

oxidizing a compound represented by the general formula [IV] into said optically active α,β-dihydroxyketone,

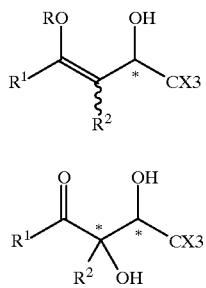

[IV]

[V]

wherein R is a lower alkyl group or —Si(R$^3$)$_3$,

R$^3$ is a lower alkyl group and three of R$^3$ may be the same or different groups, R$^1$ is a lower alkyl group or a substituted or unsubstituted phenyl group, R$^2$ is hydrogen atom or a lower alkyl group or a substituted or unsubstituted phenyl group, R$^2$ is hydrogen atom or a lower alkyl group or a substituted or unsubstituted phenyl group, or R$^1$ and R$^2$ are combined to form an alkylene group so that the compound represented by the general formula [IV] is a cycloalkylene or the compound represented by general formula [IV] is a cyclic compound, and X is hydrogen, fluorine, chlorine or bromine with a proviso that three of said X may be the same or different atoms, but are not hydrogen at the same time.

14. A method according to claim 13, wherein said oxidizing is conducted by an oxidizing agent.

15. A method according to claim 14, wherein said oxidizing agent is methachloroperbenzoic acid.

16. A method according to claim 14, wherein said oxidizing agent is in an amount of at least one equivalent per equivalent of said compound.

17. An optically active α,β-dihydroxyketone represented by the general formula [V],

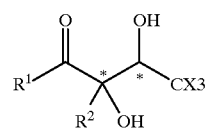

[V]

wherein R$^1$ is a lower alkyl group or a substituted or unsubstituted phenyl group, R$^2$ is hydrogen atom or a lower alkyl group or a substituted or unsubstituted phenyl group, or R$^1$ and R$^2$ are combined to form an alkylene group so that the compound represented by the general formula [IV] is a cyclic compound, and X is hydrogen, fluorine, chlorine, or bromine with a proviso that three of said X may be the same or different atoms, but are not hydrogen at the same time.

* * * * *